(12) United States Patent
Jung et al.

(10) Patent No.: US 8,394,595 B2
(45) Date of Patent: Mar. 12, 2013

(54) LAB-ON-A-CHIP AND METHOD OF DRIVING THE SAME

(75) Inventors: Moon-Youn Jung, Daejeon (KR); Dong-Ho Shin, Daejeon (KR); Minsuk Jeong, Jeongeup-si (KR); Sanghee Kim, Daejeon (KR); Hye-Yoon Kim, Daejeon (KR); Seon-Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 166 days.

(21) Appl. No.: 12/738,683

(22) PCT Filed: Oct. 17, 2008

(86) PCT No.: PCT/KR2008/006135
§ 371 (c)(1),
(2), (4) Date: May 18, 2010

(87) PCT Pub. No.: WO2009/051432
PCT Pub. Date: Apr. 23, 2009

(65) Prior Publication Data
US 2010/0227419 A1 Sep. 9, 2010

(30) Foreign Application Priority Data
Oct. 17, 2007 (KR) ................. 10-2007-0104589

(51) Int. Cl.
*G01N 33/53* (2006.01)
(52) U.S. Cl. ........................................... 435/7.1
(58) Field of Classification Search .............. None
See application file for complete search history.

(56) References Cited

U.S. PATENT DOCUMENTS

| | | | | |
|---|---|---|---|---|
| 4,888,484 A * | 12/1989 | Harvey | ................. | 250/343 |
| 5,135,719 A * | 8/1992 | Hillman et al. | ............... | 422/534 |
| 5,458,852 A * | 10/1995 | Buechler | ................. | 422/417 |
| 6,555,061 B1 * | 4/2003 | Leong et al. | ................. | 422/412 |
| 6,696,024 B1 * | 2/2004 | Leichner et al. | ............. | 422/503 |
| 6,905,882 B2 | 6/2005 | Buechler | | |
| 7,238,324 B2 | 7/2007 | Ko et al. | | |
| 2003/0085659 A1 * | 5/2003 | Overmann et al. | ............. | 315/32 |
| 2009/0082219 A1 * | 3/2009 | Ermantraut et al. | ........... | 506/10 |

FOREIGN PATENT DOCUMENTS

| | | |
|---|---|---|
| KR | 1020040013731 A | 2/2004 |
| KR | 1020060034390 A | 4/2006 |
| KR | 1020060053183 A | 5/2006 |
| KR | 1020070099233 A | 10/2007 |
| WO | WO 2006/022495 A1 | 3/2006 |

OTHER PUBLICATIONS

International Search Report for PCT/KR2008/006135 filed on Oct. 17, 2008.
Written Opinion of the International Searching Authority for PCT/KR2008/006135 filed on Oct. 17, 2008.

* cited by examiner

*Primary Examiner* — N. C. Yang
*Assistant Examiner* — Richard Moerschell

(57) ABSTRACT

Provided is a lab-on-a-chip. The lab-on-a-chip includes a first region where a lower substrate and an upper substrate are bonded to each other, a second region where the lower and upper substrates are not bonded, and a gap adjusting member disposed at an end of the second region that is opposite to a boundary between the first and second regions, the gap adjusting member being configured to adjust a gap between the first and second substrates to control a capillary force.

17 Claims, 6 Drawing Sheets

[Fig. 1]
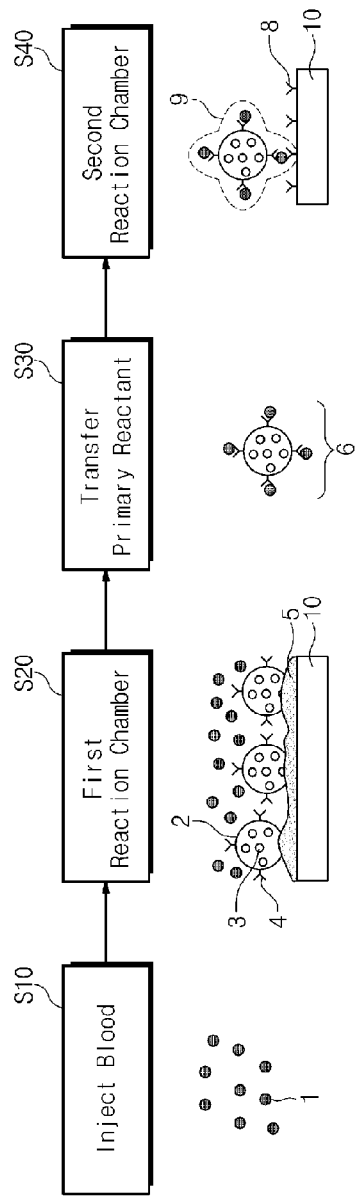
[Fig. 2]
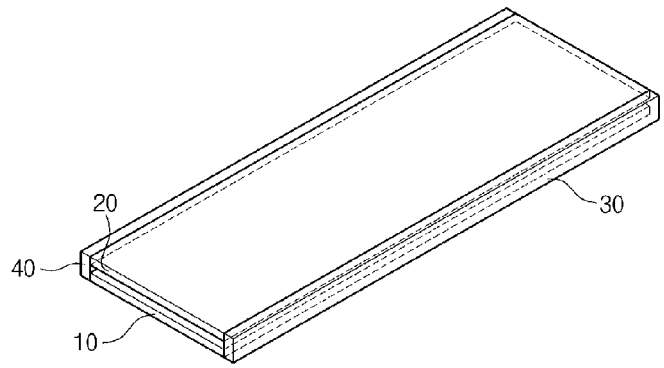

[Fig. 3]
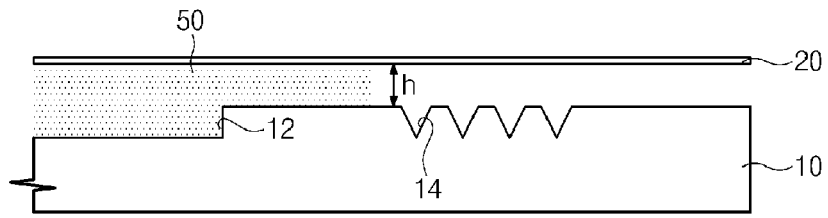
[Fig. 4]
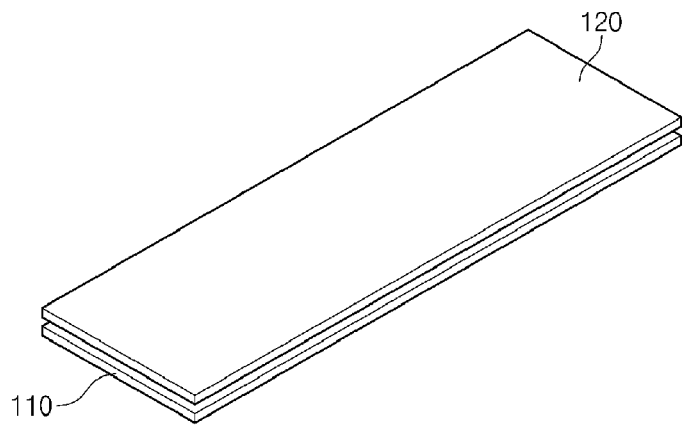
[Fig. 5]
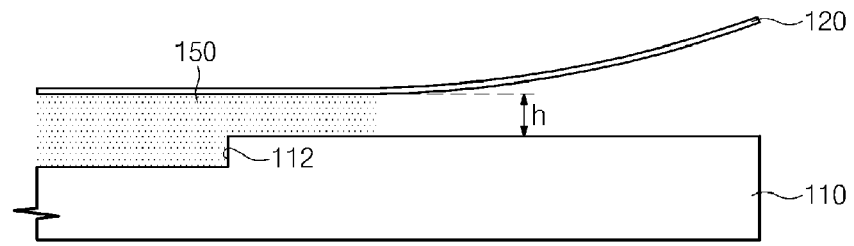
[Fig. 6]
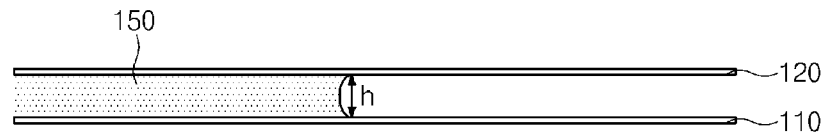
[Fig. 7]
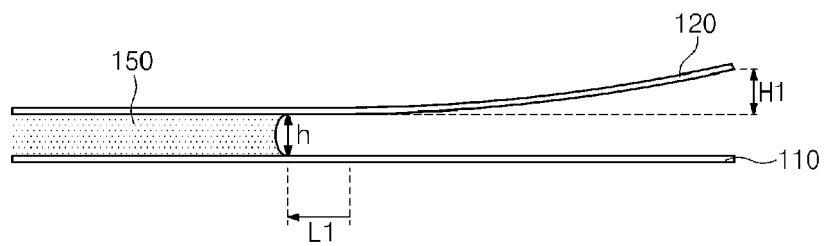

[Fig. 8]
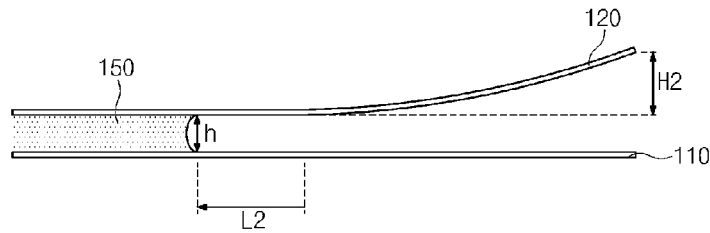
[Fig. 9]
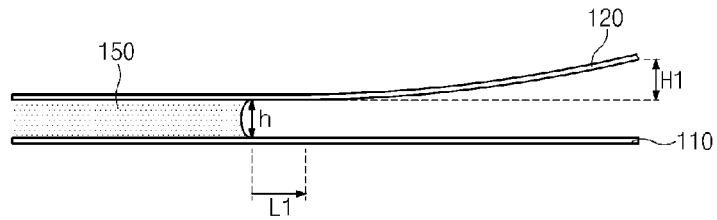
[Fig. 10]
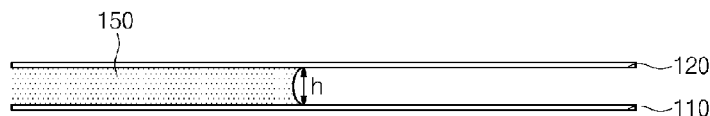
[Fig. 11]
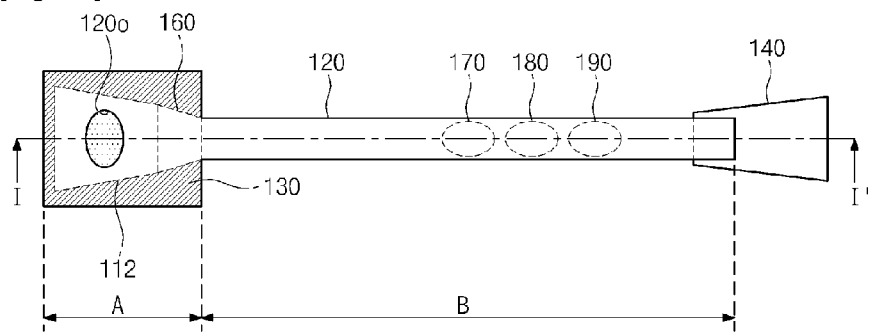
[Fig. 12]
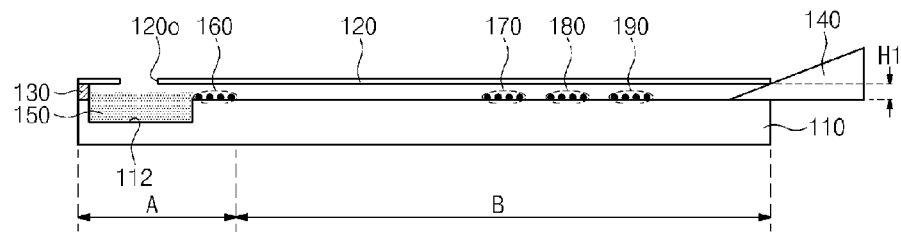
[Fig. 13]
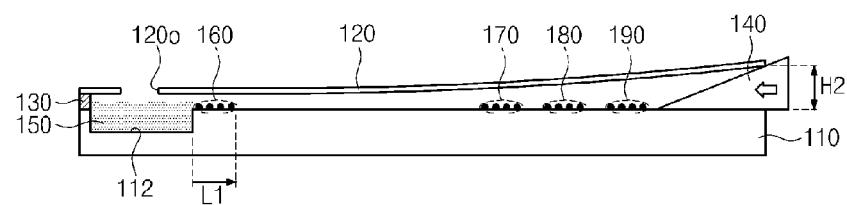

[Fig. 14]
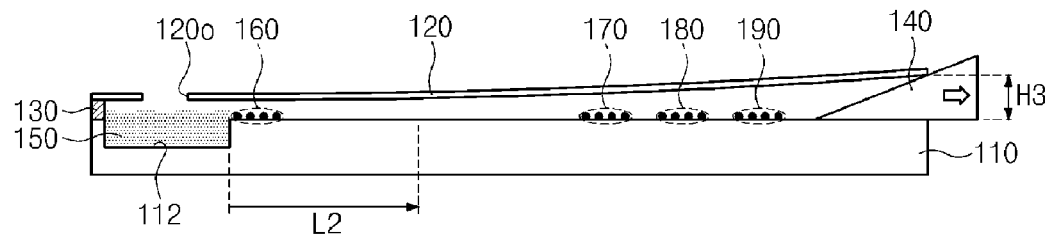
[Fig. 15]
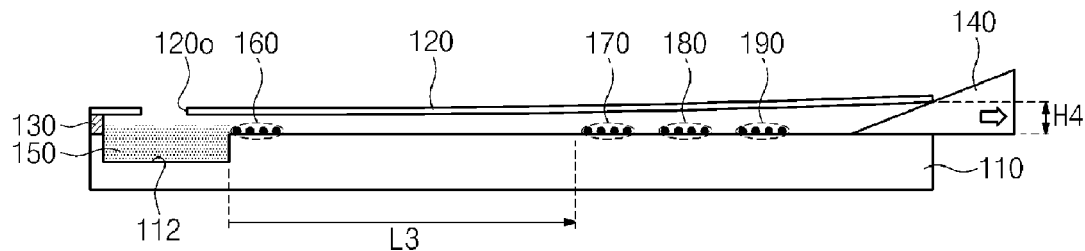
[Fig. 16]
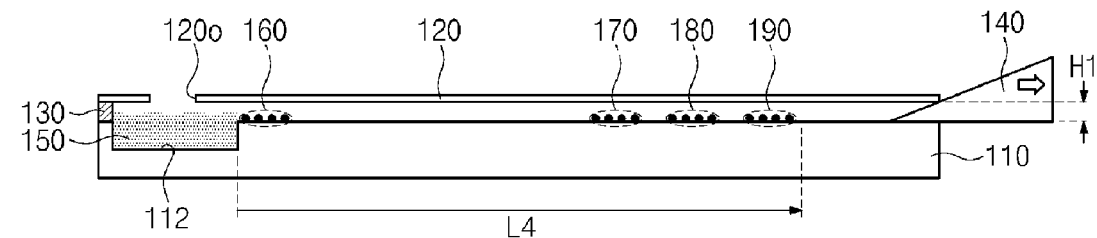
[Fig. 17]
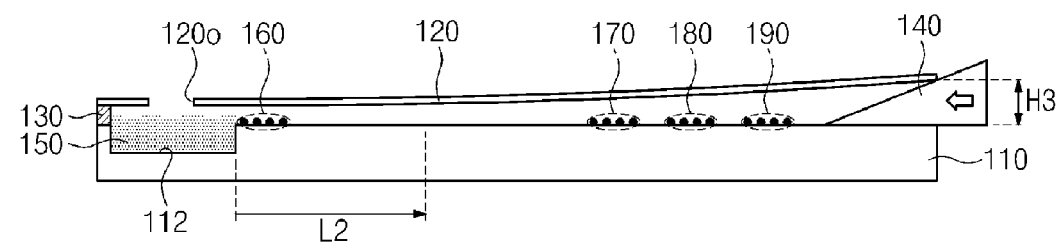
[Fig. 18]
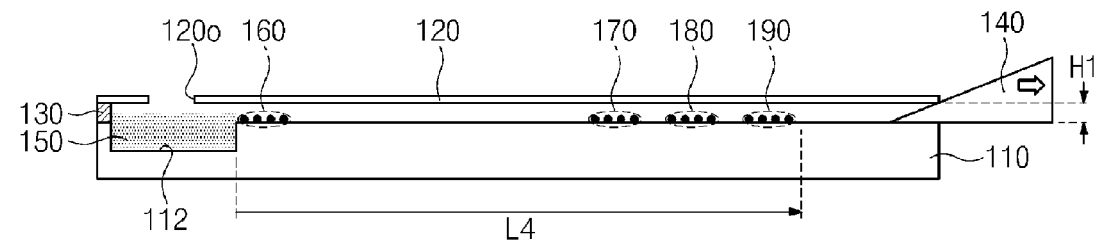

[Fig. 19]
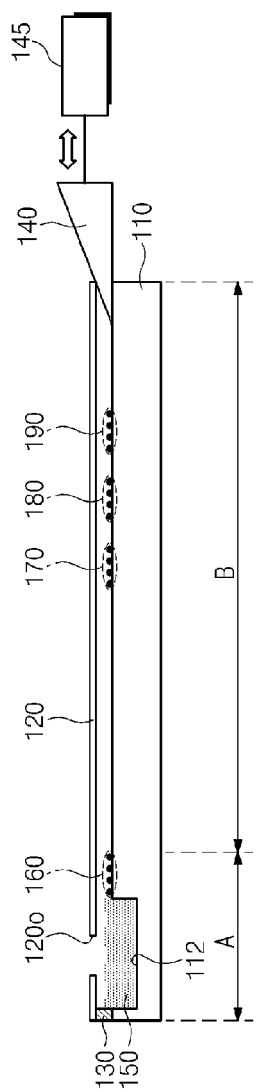
[Fig. 20]
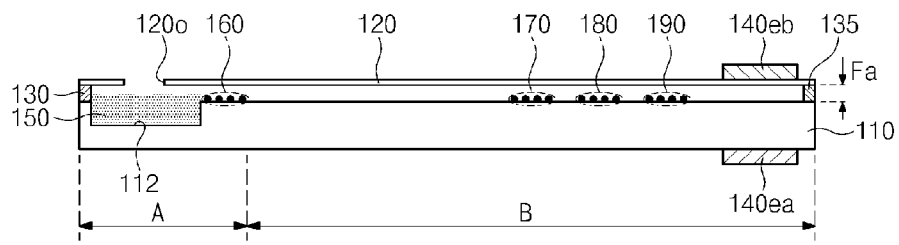
[Fig. 21]
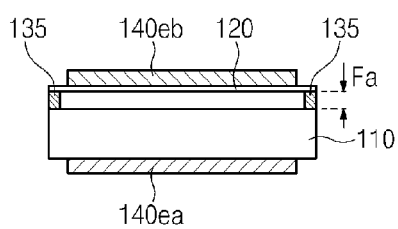

[Fig. 22]
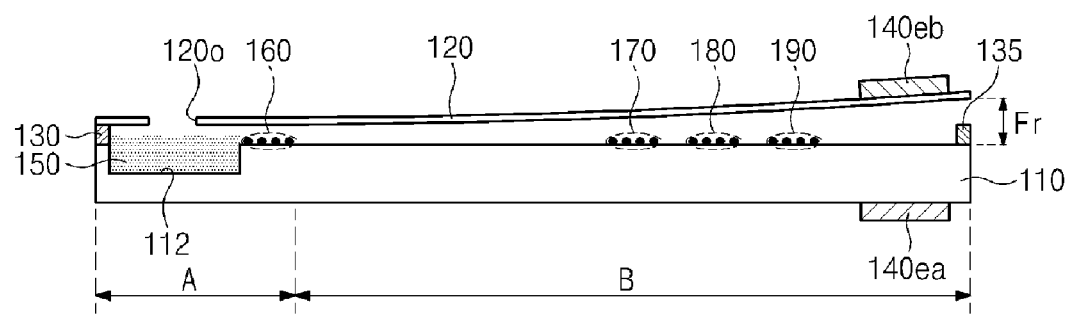
[Fig. 23]
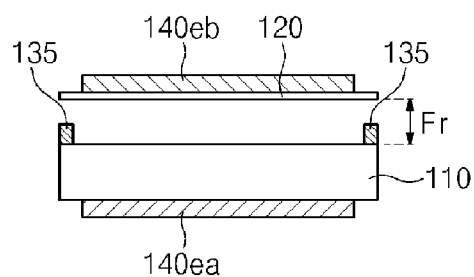

LAB-ON-A-CHIP AND METHOD OF DRIVING THE SAME

TECHNICAL FIELD

The present disclosure relates to a lab-on-a-chip, and more particularly, to a capillary force adjustable lab-on-a-chip and a method of driving the same.

The present invention has been derived from a research undertaken as a part of the information technology (IT) development business by Ministry of Information and Communication and Institute for Information Technology Advancement, Republic of Korea (Project management No.: 2005-S-007-02, Project title: Ubiquitous health care module system).

BACKGROUND ART

With the development of human society, chemical industries have been continually developed, thus necessitating the development of chemical analysis technology. The chemical analysis technology commonly designates a method used to identify and detect a specific material, and find out the chemical composition.

For rapid and accurate chemical analysis, a chemical analysis apparatus is under development to automatically perform the chemical analysis instead of a manual chemical analysis that depends on an individual experimenter. In such a chemical analysis apparatus, only if a collected sample is supplied to the apparatus, a total analysis procedure is automatically performed in one system. That is, operations of mixing the sample with reagents, reacting them for a predetermined time, transferring a reactant to a detector, and outputting a signal in proportion to the concentration of a target substance as an electrical or optical signal are automatically carried out in one measuring system.

Recently, an innovative apparatus where an automatic analysis apparatus is finely implemented in a very small-sized chip has been developed, which is called a lab-on-a-chip. The lab-on-a-chip has a fine fluid channel through which a fluid sample is introduced, and then various operations for chemical analysis such as operations of mixing and reacting the fluid sample with reagents, and detecting the reactant are performed within one lab-on-a-chip. The use of the lab-on-a-chip for chemical analysis allows the chemical analysis procedure to be very simplified, and further a pre- or post-treatment before or after the chemical analysis can be omitted because the lab-on-a-chip used once is discarded. A protein lab-on-a-chip or a DNA lab-on-a-chip is put into practical use and being widely used. Herein, the protein lab-on-a-chip is an apparatus of analyzing and measuring a specific protein in blood, and the DNA lab-on-a-chip is an apparatus of analyzing a specific deoxyribonucleic acid (DNA) in a sample.

FIG. 1 is a flowchart and related concept views illustrating a chemical analysis procedure in a lab-on-a-chip. Herebelow, descriptions will be made on a procedure of separating a blood cell from blood and a procedure of analyzing a specific protein included in a portion of a blood plasma component.

Referring to FIG. 1, a blood is injected into a lab-on-a-chip (S10). A biomarker protein 1 in the blood injected into the lab-on-a-chip moves to a first reaction chamber.

The biomarker protein 1 included in a fluid reacts with a carrier particle 2 in the first reaction chamber (S20). Herein, the carrier particle 2 includes a fluorescent substance 3 and a primary antibody 4. The carrier particle 2 may be nanometers or micrometers in size. The carrier particle 2 may be fixed by a scaffold 5, which is provided on a lower substrate 10 of the first reaction chamber and composed of a mucous substance having an adhesive force. A primary antigen-antibody reactant 6 is formed through the primary antigen-antibody reaction between the biomarker protein 1 included in the fluid and the primary antibody 4 included in the carrier particle 2.

The primary antigen-antibody reactant 6 is transferred according as the fluid flows (S30). The primary antigen-antibody reactant 6 transferred by the flow of the fluid reacts with a secondary antibody 8 in a second reaction chamber. A secondary antigen-antibody reactant 9 is formed through the secondary antigen-antibody reaction between the biomarker protein 1 included in the primary antigen-antibody reactant 6 and the secondary antibody 8. The fluorescent image caused by the fluorescent substance 3 contained in the carrier particle 2 is analyzed by irradiating light onto the secondary antigen-antibody reactant 9. Therefore, it is possible to analyze whether a specific protein is contained or not in blood, and the amount of the specific protein.

FIGS. 2 and 3 are conceptual perspective and sectional views illustrating a typical capillary force lab-on-a-chip.

Referring to FIGS. 2 and 3, the typical capillary force lab-on-a-chip includes a lower substrate 10, an upper substrate 20, and side substrates 30 and 40. The lower substrate 10 and the upper substrate 20 are arranged in such a way to have a constant gap h therebetween, thereby forming a capillary. Herein, the mark h means a threshold gap, i.e., the maximum height allowing the capillary to have a capillary force. The capillary forces respectively exist on inner surfaces of the lower substrate 10, the upper substrate and the side substrates 30 and 40.

The lower substrate 10 includes a filter part 12 and hydrophobic grooves 14. The filter part 12 filters an unnecessary component of a fluid sample 50, and passes a specific component selectively. The hydrophobic grooves 14 serve as a timegate delaying the flow of the fluid containing the specific component of the fluid specimen 50. The hydrophobic grooves 14 are obtained through surface-treatment. For example, surfaces of the grooves formed in the lower substrate 10 are surface-treated with hydrophobic substances. Differently from the drawings, the timegate may be achieved by modifying the shape of a channel through which the fluid flows. Such a timegate is used to delay the flow of the fluid to thereby increase the reactivity between the specific component included in the fluid and a reagent.

In the capillary force lab-on-a-chip having a timegate using the hydrophobic grooves, as an inflow rate of the fluid containing the specific component becomes fast, the fluid makes the hydrophobic groove to be wet or the hydrophobicity of the surface of the hydrophobic groove weakened due to the introduction of moisture. Resultantly, the hydrophobic groove does not perform its function, i.e., a timegate function, and thus a portion of the specific component included in the fluid does not react well with the reagent to be used for analysis.

Furthermore, in the capillary force lab-on-a-chip having the timegate using a shape modification of a fluid channel, the shape of the fluid channel is too complicated, which leads to a difficulty in fabrication. Also, the complicated shape of the fluid channel makes the channel length to be increased, thus causing a total size of the capillary force lab-on-a-chip to be increased.

In addition, since the timegate using the shape modification of the fluid channel or the hydrophobic grooves plays only a role in delaying the flow of the fluid, it is difficult to precisely control the reactivity between the specific component contained in the fluid specimen and the reagent.

DISCLOSURE OF INVENTION

Technical Problem

The present invention provides a capillary force lab-on-a-chip capable of freely controlling a reaction time between a fluid sample to be analyzed and a reagent by artificially adjusting the flow of a microfluid.

The present invention also provides a method of driving a capillary force lab-on-a-chip that can freely control a reaction time between a fluid sample to be analyzed and a reagent by artificially adjusting the flow of a microfluid.

Technical Solution

Embodiments of the present invention provide lab-on-a-chips including: a first region where a first substrate and a second substrate are bonded; a second region where the first and second substrates are not bonded; and a gap adjusting member disposed at an end of the second region that is opposite to a boundary between the first and second regions, the gap adjusting member being configured to adjust a gap between the first and second substrates to control a capillary force.

In some embodiments, at least one of the first and second substrates includes a flexible substrate.

In other embodiments, the first substrate of the first region includes a filter part and a first reaction part.

In still other embodiments, the second substrate of the first region includes a blood injection hole.

In even other embodiments, the filter filters blood cells of blood and passes blood plasma component only.

In yet other embodiments, the first reaction part includes a primary antibody that reacts with a blood plasma component of blood to form a primary antigen-antibody reactant.

In further embodiments, both sides of the first and second substrates of the second region are exposed.

In still further embodiments, the first substrate of the second region includes at least one of second reaction parts.

In even further embodiments, the second reaction part includes a secondary antibody that reacts with the primary antigen-antibody reactant to form a secondary antigen-antibody reactant.

In yet further embodiments, the gap adjusting member has a shape of a wedge of which one portion is interposed between the first and second substrates.

In other embodiments, the gap adjusting member moves in a left direction or a right direction by a step motor to adjust a gap between the first and second substrates at the end of the second region.

In still other embodiments of the present invention, the gap adjusting member includes a pair of electromagnets that are respectively provided on the first and second substrates at the end of the second region, the pair of electromagnets facing the gap between the first and second substrates.

In even other embodiments of the present invention, the gap adjusting member adjusts the gap between first and second substrates at the end of the second region by an attractive force and a repulsive force between the pair of the electromagnets.

In yet other embodiments, the lab-on-a-chips further include a support member interposed between the first and second substrates at the end of the second region, and maintaining the gap between the first and second substrates to be minimized.

In further embodiments of the present invention, methods of driving a lab-on-a-chip include: preparing the lab-on-a-chip including a first region where a first substrate and a second substrate are bonded, and a second region where the first and second substrates are not bonded; and controlling fluid flow in the second region by adjusting a gap between the first and second substrates at an end of the second region corresponding to a boundary between the first and second regions.

In still further embodiments, the fluid flow includes progression, retrogression from the first region to the second region, or/and standstill.

In even further embodiments, the second region includes at least one reaction part, and the controlling of the fluid flow in the second region includes controlling a reaction between the fluid and the reaction part.

Advantageous Effects

According to embodiments of the present invention, a capillary force lab-on-a-chip can change the capillary force freely, allowing the flow of a microfluid to be controlled. Accordingly, it is possible to provide a capillary force lab-on-a-chip with enhanced performance, which can freely control a reaction time between a fluid sample to be analyzed and a reagent.

BRIEF DESCRIPTION OF THE DRAWINGS

The accompanying figures are included to provide a further understanding of the present invention, and are incorporated in and constitute a part of this specification. The drawings illustrate exemplary embodiments of the present invention and, together with the description, serve to explain principles of the present invention. In the figures:

FIG. 1 is a flowchart and related concept views illustrating a chemical analysis procedure in a lab-on-a-chip;

FIGS. 2 and 3 are conceptual perspective and sectional views illustrating a typical capillary force lab-on-a-chip;

FIGS. 4 and 5 are conceptual perspective and sectional views illustrating a capillary force lab-on-a-chip according to an embodiment of the present invention;

FIGS. 6 through 10 are conceptual sectional views illustrating an operation principle of the capillary force lab-on-a-chip according to an embodiment of the present invention;

FIG. 11 is a plan view illustrating a capillary force lab-on-a-chip according to an embodiment of the present invention;

FIG. 12 through 18 are sectional views taken along line I-I of FIG. 11;

FIG. 19 is a sectional view illustrating a capillary force lab-on-a-chip according to an embodiment of the present invention; and FIGS. 20 through 23 are sectional views and side views illustrating an operation principle of a capillary force lab-on-a-chip according to another embodiment of the present invention.

MODE FOR THE INVENTION

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Since following descriptions will be made according to preferred embodiments, reference numerals or symbols given in the sequence of illustrations are not limited to that sequence. In the figures, the dimensions of layers and regions are exaggerated for clarity of illustration. It will also be understood that when a layer (or film) is referred to as being on another layer or substrate, it can be directly on the other layer or substrate, or intervening layers may also be present.

FIGS. 4 and 5 are conceptual perspective and sectional views illustrating a capillary force lab-on-a-chip according to an embodiment of the present invention.

Referring to FIGS. 4 and 5, the capillary force lab-on-a-chip may include a lower substrate 110, and an upper substrate 120. The lower and upper substrates 110 and 120 are disposed in such a way to have a constant gap h therebetween, thereby forming a capillary. The capillary force may exist on opposite surfaces of the lower and upper substrate 110 and 120.

Referring to FIG. 4, the capillary phenomenon may exist even though both sidewalls of the capillary are exposed. If both sidewalls of the capillary are exposed, the capillary force may disappear at both sidewalls but a cohesive force itself of a fluid sample 150 may exit. That is, since the capillary force is relatively greater than the cohesive force of the fluid sample 150 at opposite surfaces of the lower and upper substrates 110 and 120, the fluid sample 150 can flow along the opposite surfaces of the lower and upper substrates 110 and 120. However, the fluid sample 150 cannot flow along the sidewalls because the capillary force does not exist on the exposed sidewalls of the capillary. As described above, the fluid sample 150 itself has the cohesive force, and thus the fluid sample 150 does not leak out from the exposed sidewalls of the capillary.

The capillary force at the opposite surfaces of the lower and upper substrates 110 and 120 is very greater than the capillary force at boundaries between the upper and lower substrates 110 and 120 and the exposed sidewalls. Therefore, it is possible to neglect the flow of the fluid sample 150 flowing along the boundaries between the upper and lower substrates 110 and 120 and the exposed sidewalls.

The lower substrate 110 includes a filter part 112. The filter part 112 filters an unnecessary component of a fluid sample 150, and selectively passes a specific component to be analyzed. At least one of the lower and upper substrates 110 and 120 may be a flexible substrate with elasticity. Preferably, the upper substrate 120 may be a flexible substrate. Accordingly, if one end of the upper substrate 120 is lifted up, the upper substrate 120 may be bended like a curved line. That is, there are two regions of which one region has a gap distance between the upper and lower substrates 110 and 120 is maintained h, and the other region has a gap distance exceeding h. Consequently, it is possible to control the capillary force of the capillary configured with the lower and upper substrates 110 and 120, which will be more fully described in FIGS. 6 through 10.

FIGS. 6 through 10 are conceptual sectional views illustrating an operation principle of the capillary force lab-on-a-chip according to an embodiment of the present invention.

Referring to FIG. 6, a channel of the capillary force lab-on-a-chip may be a capillary through which the fluid sample 150 flows by the capillary force due to the gap distance h between the lower and upper substrates 120. In this way, the fluid sample 150 can continuously flow in a right direction along the capillary configured with the lower and upper substrates 110 and 120 if the gap distance between the lower and upper substrates 110 and 120 is constantly maintained h.

Referring to FIG. 7, if one end of the upper substrate is lifted up to increase the gap distance to h+H1 from h while the other end of the capillary is maintained to have the gap distance h between the lower and upper substrates 110 and 120, the fluid sample 150 retrogresses to a distance L1. This is because the threshold gap of the capillary generating the capillary force is h. If the gap of the capillary is equal to h or less, the capillary may have a capillary force. On the contrary, if the gap of the capillary is greater than a threshold gap h or more, the capillary may loose its capillary force.

Referring to FIG. 8, when the one end of the upper substrate 120 of the capillary is more lifted up to increase the gap distance between the first and second substrates 110 and 120 to h+H2 from h+H1, the fluid sample 150 more retrogresses to a distance L2.

Referring to FIG. 9, when the one end of the upper substrate 120 of the capillary is let down to decrease the gap distance between the first and second substrates 110 and 120 to h+H1 from h+H2, the fluid sample 150 progresses to the distance L1.

Referring to FIG. 10, when the one end of the upper substrate 120 of the capillary is more let down to decrease the gap distance between the first and second substrates 110 and 120 to h from h+H1, the fluid sample 150 progresses to the position shown in FIG. 6. Therefore, the fluid sample 150 can flow by virtue of the capillary force of the capillary. That is, the fluid sample 150 can continuously flow in a right direction along the capillary configured with the lower and upper substrates 110 and 120.

As illustrated in FIGS. 6 through 10, a change in a geometrical shape of the capillary leads to a change in a capillary force. That is, if at least one of the upper and lower substrates 120 and 110 constituting the capillary is a flexible substrate with elasticity, it is possible to finely control the flow of the fluid sample 150, e.g., progression, retrogression and standstill by adjusting the capillary force of the capillary. Accordingly, a reaction time between the fluid sample to be analyzed and a reagent can be controlled freely.

FIG. 11 is a plan view illustrating a capillary force lab-on-a-chip according to an embodiment of the present invention. FIG. 12 through 18 are sectional views taken along line I-I? of FIG. 11. Herebelow, descriptions will be made on a protein lab-on-a-chip of separating blood cells from blood and analyzing a specific protein contained in a portion of a blood plasma.

Referring to FIGS. 5 and 12, a capillary force lab-on-a-chip may include a first region A where a lower substrate 110 and an upper substrate 120 are bonded to each other, a second region B where the lower and upper substrates 110 and 120 are not bonded, a gap adjusting member 140. The gap adjusting member 140 is disposed at one end of the second region B that is opposite to a boundary between the first region A and the second region B, and is configured to adjust a gap between the lower substrate 110 and the upper substrate 120.

The lower and upper substrates 110 and 120 of the first region A may be bonded to each other by means of a bonding member 130. The bonding member 130 may be used to airtightly seal the first region A. The lower substrate 110 of the first region A may include a filter part 112 and a first reaction part 160. The filter part 112 is formed such that its bottom surface is lower than a bottom surface of the first reaction part 160, and therefore, the filter part 112 may serve as a fluid reservoir. The filter part 112 may play a role in filtering blood cells from blood 150 and passing a fluid containing a blood plasma component. The first reaction part 160 may include a primary antibody (see dots of reference numeral 160), which reacts with the blood plasma component of the blood 150 to form a primary antigen-antibody reactant (see reference numeral 6 of FIG. 1). The upper substrate 120 of the first region A may have a blood injection hole 120o for injecting the blood 150 into the lab-on-a-chip. The blood cells are filtered from the blood 150 while the injected blood 150 passes through the filter part 112. The fluid containing the blood plasma component can flow into the first reaction part 160 by the capillary force of the capillary configured with the lower and upper substrates 110 and 120.

Both side parts of the lower and upper substrates 110 and 120 in the second region B may be exposed, which has been already described with reference to FIGS. 4 and 5. The exposed side parts of the lower and upper substrates 110 and 120 in the second region B may be intended to adjust a gap between the lower and upper substrates 110 and 120. The lower substrate 110 of the second region B may include at least one of reaction parts 170, 180 and 190. The second reaction part 170, 180 and/or 190 may include a secondary antibody (see dots of reference numerals 170, 180 and/or 190), which reacts with the primary antigen-antibody reactant to produce a secondary antigen-antibody reactant (see reference numeral 9 of FIG. 1). The secondary antibody of the second reaction part 170, 180 and/or 190 may provide different antigen-antibody reactions, respectively. Consequently, it is also possible to simultaneously perform analysis for various antigens.

The gap adjusting member 140 may have a shape of a wedge of which one portion is interposed between the lower substrate 110 and the upper substrate 120. The gap between the lower substrate 110 and the upper substrate 120 at an end of the second region B can be freely controlled by shifting the wedge-shaped gap adjusting member 140 in a right or left direction between the lower and upper substrates 110 and 120 at the one end of the second region B.

Referring to FIG. 12, a channel of the capillary force lab-on-a-chip may be a capillary through which the fluid sample 150 flows in a right direction by the capillary force due to the gap distance H1 between the lower and upper substrates 110 and 120. In this way, the fluid sample 150 can continuously flow in a right direction along the capillary configured with the lower and upper substrates 110 and 120 if the gap distance between the lower and upper substrates 110 and 120 is maintained H1.

Referring to FIG. 13, if the gap adjusting member 140 shifts in a left direction, the upper substrate 120 at the end of the second region B is lifted up to increase the gap distance between the lower and upper substrates 110 and 120 to H2 from H1. Resultingly, a fluid (not shown) containing a blood plasma component, which flows into the second region B, can retrogress to a distance L1 at which the first reaction part 160 is disposed. This may allow a primary antigen-antibody reaction between the blood plasma component contained in the fluid where the blood cell of the blood 150 is filtered, and the primary antibody of the first reaction part 160 to be sufficiently generated. Therefore, a primary antigen-antibody (not shown) may be produced.

Referring to FIG. 14, if the gap adjusting member 140 shifts in a right direction, the upper substrate 120 at the end of the second region B is let down to decrease the gap distance between the lower and upper substrates 110 and 120 to H3 from H2. Accordingly, the fluid containing the primary antigen-antibody reactant and an unreacted blood plasma component can progress to a distance L2. This may transfer the primary antigen-antibody reactant produced in the first reaction part 160.

Referring to FIG. 15, if the gap adjusting member 140 further shifts in the right direction, the upper substrate 120 at the end of the second region B is more let down to decrease the gap distance between the lower and upper substrates 110 and 120 to H4 from H3. Accordingly, the fluid containing the primary antigen-antibody reactant and the unreacted blood plasma component can further progress up to a distance L3. The above-described procedure illustrated in FIGS. 13 through 15 may be repetitively performed so as to form the unreacted blood plasma component contained in the fluid as the primary antigen-antibody reactant.

Referring to FIG. 16, if the upper substrate 120 at the end of the second region B is completely let down by further shifting the wedge-shaped gap adjusting member 140 in the right direction, the gap distance between the lower and upper substrates 110 and 120 is decreased to H1 from H4. Accordingly, the fluid containing the primary antigen-antibody reactant and the unreacted blood plasma component can further progress up to a distance L4 at which the second reaction part 170, 180 and/or 190 is disposed. This may allow a secondary antigen-antibody reaction between the primary antigen-antibody reactant produced in the first reactant 160 and the secondary antibody to be generated. Therefore, the secondary antigen-antibody reactant (not shown) may be produced.

Referring to FIG. 17, if the gap adjusting member 140 shifts in a left direction again, the upper substrate 120 at the end of the second region B is lifted up again to thereby increase the gap distance between the lower and upper substrates 110 and 120 to H3 from H1. Consequently, the fluid containing the secondary antigen-antibody reactant, the unreacted primary antigen-antibody reactant and the unreacted blood plasma component can retrogress to the distance L2 again.

Referring to FIG. 18, if the gap adjusting member 140 shifts in the right direction again, the upper substrate 120 at the end of the second region B is let down to decrease the gap distance between the lower and upper substrates 110 and 120 to H1 from H3 again. Consequently, the fluid containing the secondary antigen-antibody reactant, the unreacted primary antigen-antibody reactant and the unreacted blood plasma component can progress to the distance L4 again. This may allow the secondary antigen-antibody reaction between the primary antigen-antibody reactant and the second body of the second reaction part 170, 180 and/or 190 to be sufficiently generated. The above-described procedure illustrated in FIGS. 16 through 18 may be repetitively performed so as to form the unreacted blood plasma component contained in the fluid as the secondary antigen-antibody reactant.

When the gap between the lower and upper substrates 110 and 120 at the end of the second region B is continually maintained H1, the fluid containing the unreacted blood plasma component and the unreacted primary antigen-antibody reactant can flow by virtue of the capillary force of the capillary.

Furthermore, when the procedure illustrated in FIGS. 16 through 18 is repeated, a noise signal, which may be generated during analysis process, may be reduced by desorbing non-specific bonding components. Since it is impossible for the typical capillary force lab-on-a-chip to change the flow direction of the fluid, it is difficult to completely desorb the non-specific bonding components. In addition, the desorption of the non-specific bonding components is greatly affected by the flow rate of the fluid. The typical capillary force lab-on-a-chip can do nothing but delay the flow of the fluid, and thus the flow rate of the fluid cannot be controlled. In contrast, the capillary force lab-on-a-chip of the present invention is advantageous in that it is possible to minimize the noise signal generated during analysis process, which significantly differs from the typical capillary force lab-on-a-chip.

As understood from FIGS. 12 through 18, the number of times of the flow such as retrogression, progression and standstill of the fluid containing the blood plasma component can be controlled if necessary. Therefore, it is possible to freely control a reaction time between the fluid containing the blood plasma component of the blood 150 to be analyzed and the primary and secondary antibodies (see dots of reference numerals 160, 170, 180 and 190).

FIG. 19 is a sectional view illustrating a capillary force lab-on-a-chip according to an embodiment of the present invention.

Referring to FIG. 19, the gap adjusting member 140 of the capillary force lab-on-a-chip may have a shape of a wedge of which one portion is interposed between the lower substrate 110 and the upper substrate 120. A step motor 145 drives the wedge-shaped gap adjusting member 140 to move in a right direction and/or a left direction between the lower and upper substrates 110 and 120 at the end of the second region B, thus making it possible to freely control the gap distance between the lower substrate 110 and the upper substrate 120 at the end of the second region B. That is, the capillary force of the capillary is controlled by the wedge-shaped gap adjusting member 140 that is driven by the step motor 145. Therefore, the reaction time between the fluid sample 150 to be analyzed and the reagent can be freely controlled.

FIGS. 20 through 23 are sectional views and side views illustrating an operation principle of a capillary force lab-on-a-chip according to another embodiment of the present invention.

Referring to FIGS. 20 and 21, the gap adjusting members 140ea and 140eb of the capillary force lab-on-a-chip may be a pair of electromagnets, which are respectively provided on the lower and upper substrates 110 and 120 at the end of the second region B. Herein, the gap adjusting members 140ea and 140eb may be arranged in such a way to face the gap between the lower and upper substrates 110 and 120. The capillary force lab-on-a-chip may further include a support member 135 configured to maintain the gap distance between the lower and upper substrates 110 and 120 at the end of the second region B minimally. The support member 135 may be disposed between the lower and upper substrates 110 and 120 at the end of the second region B. The support member 135 may be used to prevent the lower and upper substrates 110 and 120 of the capillary from contacting each other.

When an attractive force Fa is exerted between the gap adjusting member 140ea and 140eb, i.e., the pair of the electromagnets, the gap distance between the lower and upper substrates 110 and 120 at the end of the second region B may be decreased.

Referring to FIGS. 22 and 23, a repulsive force Fr is exerted between the gap adjusting member 140ea and 140eb, i.e., the pair of the electromagnets, the gap distance between the lower and upper substrates 110 and 120 at the end of the second region B may be increased.

According to the direction of current supplied to the pair of the electromagnets, the attractive force or the repulsive force may be exerted between the pair of electromagnets. In addition, the intensity of the attractive or repulsive force generated between the pair of electromagnets can be adjusted depending on the intensity of the current supplied to the pair of electromagnets. That is, the capillary force of the capillary is controlled by virtue of the gap adjusting members 140ea and 140eb configured with the pair of electromagnets so that it is possible to freely control the flow such as retrogression, progression, and standstill of the fluid sample 150. This may allow the reaction time between the fluid sample 150 to be analyzed and the reagent to be freely controlled.

The capillary force lab-on-a-chip according to the embodiments of the present invention is configured to control the gap of the capillary so that the flow of the microfluid can be freely controlled. Consequently, it is possible to realize a capillary force lab-on-a-chip with enhanced performance that can freely control the reaction time between the fluid sample to be analyzed and the reagent, and a method of driving the capillary force lab-on-a-chip.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. A lab-on-a-chip comprising:
   a first region where a first substrate and a second substrate are bonded, the first region including an inlet for receiving a sample fluid;
   a second region where the first and second substrates are not bonded, the second region including a fluid pathway configured to provide the sample fluid from the first region to the second region, wherein the first region is coupled to a first end of the second region; and
   a gap adjusting member disposed at a second end of the second region opposing the first end of the second region, the gap adjusting member being configured to adjust a gap between the first and second substrates by adjusting one of the first substrate or the second substrate relative to the other of the first substrate or the second substrate in order to vary a capillary force between the first substrate and the second substrate.

2. The lab-on-a-chip of claim 1, wherein at least one of the first and second substrates comprises a flexible substrate.

3. The lab-on-a-chip of claim 1, wherein the first substrate of the first region comprises a filter part and a first reaction part.

4. The lab-on-a-chip of claim 3, wherein the second substrate of the first region comprises the inlet, and wherein the inlet serves as a blood injection hole.

5. The lab-on-a-chip of claim 3, wherein the filter is adapted to filter blood cells of blood and pass blood plasma components only.

6. The lab-on-a-chip of claim 3, wherein the first reaction part comprises a primary antibody that reacts with a blood plasma component of blood to form a primary antigen-antibody reactant.

7. The lab-on-a-chip of claim 1, wherein both sides of the first and second substrates of the second region are exposed.

8. The lab-on-a-chip of claim 3, wherein the first substrate of the second region comprises at least one second reaction part.

9. The lab-on-a-chip of claim 8, wherein the second reaction part comprises a secondary antibody that reacts with the primary antigen-antibody reactant to form a secondary antigen-antibody reactant.

10. The lab-on-a-chip of claim 1, wherein the gap adjusting member has a shape of a wedge, wherein an acute portion of the wedge is interposed between the first and second substrates.

11. The lab-on-a-chip of claim 10, further comprising a step motor configured to drive the gap adjusting member in any of a first direction towards the first end of the second region and a second direction away from the first end of the second region to adjust the gap between the first and second substrates.

12. The lab-on-a-chip of claim 1, wherein the gap adjusting member comprises a pair of electromagnets that are respectively provided on the first and second substrates at the end of the second region, the pair of electromagnets facing the gap between the first and second substrates.

13. The lab-on-a-chip of claim 12, wherein the gap adjusting member adjusts the gap between first and second substrates at the end of the second region by an attractive force and a repulsive force between the pair of the electromagnets.

14. The lab-on-a-chip of claim 12, further comprising a support member interposed between the first and second substrates at the end of the second region, and maintaining the gap between the first and second substrates to be minimized.

15. A method of driving a lab-on-a-chip, the method comprising:
    preparing the lab-on-a-chip including a first region where a first substrate and a second substrate are bonded, and a second region where the first and second substrates are not bonded; and
    controlling fluid flow in the second region by using a gap adjusting member, the gap adjusting member being configured to adjust a gap between the first and second substrates by adjusting one of the first substrate or the second substrate relative to the other of the first substrate or the second substrate in order to vary a capillary force between the first substrate and the second substrate,
    wherein the first region includes an inlet for receiving a sample fluid,
    wherein the second region includes a fluid pathway configured to provide the sample fluid from the first region to the second region,
    wherein the first region is coupled to a first end of the second region, and
    wherein the gap adjusting member is disposed at a second end of the second region opposing the first end of the second region.

16. The method of claim 15, wherein the fluid flow includes any of progression of the sample fluid from the first region towards the second region, retrogression of the sample fluid towards the first region, and standstill.

17. The method of claim 15, wherein the second region comprises at least one reaction part, and the controlling of the fluid flow in the second region comprises controlling a reaction between the sample fluid and the reaction part.

* * * * *